United States Patent [19]

Sawada et al.

[11] 3,950,514
[45] Apr. 13, 1976

[54] **ANTIBIOTIC TM-481 DERIVED FROM MICROORGANISM OF THE *STREPTOMYCES RIBOSIDIFICUS* GROUP**

[75] Inventors: Jiro Sawada, Kodaira; Sadafumi Omura, Saitama; Michinori Shibata, Saitama; Sadao Machida, Saitama, all of Japan

[73] Assignee: Taisho Pharmaceutical Co., Ltd., Tokyo, Japan

[22] Filed: Sept. 4, 1974

[21] Appl. No.: 503,165

[30] Foreign Application Priority Data
Sept. 5, 1973 Japan.............................. 48-99977

[52] U.S. Cl. ............................................. 424/121
[51] Int. Cl.² ......................................... A61K 35/00
[58] Field of Search..................................... 424/121

[56] References Cited
UNITED STATES PATENTS

| | | | |
|---|---|---|---|
| 3,159,540 | 12/1964 | Kawaguchi et al. ................. | 424/121 |
| 3,365,362 | 1/1968 | Mancy et al. ........................ | 424/121 |

*Primary Examiner*—Albert T. Meyers
*Assistant Examiner*—Daren M. Stephens
*Attorney, Agent, or Firm*—Wenderoth, Lind & Ponack

[57] ABSTRACT

A new polyether group antibiotic, TM-481, having the estimated empirical formula $C_{42-45}H_{71-75}O_{14-15}$ Na and possessing an antibacterial activity against pathogenic microorganisms, particularly Gram-positive bacteria is obtained by culturing a TM-481 producing microorganism of the *Streptomyces ribosidificus* group in a nutrient medium therefor.

5 Claims, 3 Drawing Figures

ANTIBIOTIC TM-481 DERIVED FROM MICROORGANISM OF THE *STREPTOMYCES RIBOSIDIFICUS* GROUP

BACKGROUND OF THE INVENTION

The following polyether group antibiotics are known previously:

nigericin — Antibiot. & Chemoth. 1, 594 (1951),

X-537A and X-206 — J. am. Chem. Soc. 73, 5295 (1951), monensin — Antimicr. Agents & chemoth. 349 (1967), grisorixin — Ann. Phytopath. 2, 555 (1970), dianemycin — Biochem. Biophys. Res. Commun. 45, 1279 (1971), salinomycin — Japanese Pat. Application No. 19620/72, A-28695A and A-28695B - Japanese Pat. application No. 129162/72 and A-204A — J. Am. Chem. Soc. 95, 3399 (1973).

Among them, A-28695A and A-28695B which are produced by a strain of *Streptomyces albus* are found to have four or three methoxy groups in the molecules, respectively. A-204A which is also produced by the same species has five methoxy groups in the molecule. On the other hand, other antibiotics amoung them do not have so many methoxy groups as these.

The present antibiotic, TM-841, produced by a microorganism of the *Streptomyces ribosidificus* group, has been found to have four methoxy groups in its molecule like A-28695A. TM-481, however, distinctly differs with A-28695A in melting point, infrared absorption spectrum, Rf value on thin layer chromatography, species of producing microorganism and so on. TM-481 of this invention is, therefore, elucidated to be a novel compound of polyether group antibiotics.

BRIEF SUMMARY OF THE INVENTION

This invention relates to a new antibiotic and to processes for its production and for purification thereof.

More particularly, this invention is concerned with a new antibiotic designated TM-481, derived from a new strain of microorganism belonging to *Streptomyces ribosidificus* as a novel and useful product, with a process for the preparation of said novel and antibiotic and moreover with a process for the purification thereof.

The object of the present invention is to obtain the product possessing antibiotic activity against pathogenic microorganisms.

It is still another object of the invention to obtain easily the new antibiotic designated TM-481 as a pure crystalline form.

The above-mentioned new antibiotic, TM-481, can be produced by cultivation of a new microorganism strain belonging to *Streptomyces ribosidificus*, and is obtainable as a pure crystal according to the process of this invention.

TM-481 is a kind of polyether group antibiotic and is useful in combatting pathogenic microorganisms, particularly Gram-positive bacteria.

Said microorganism strain belonging to *Streptomyces ribosidificus* and producing TM481, was isolated from a soil sample and was designated as *Streptomyces ribosidificus* TM-481 (ATCC No. 31051) by the applicants.

DETAILED DESCRIPTION OF THE INVENTION

Figure 1:
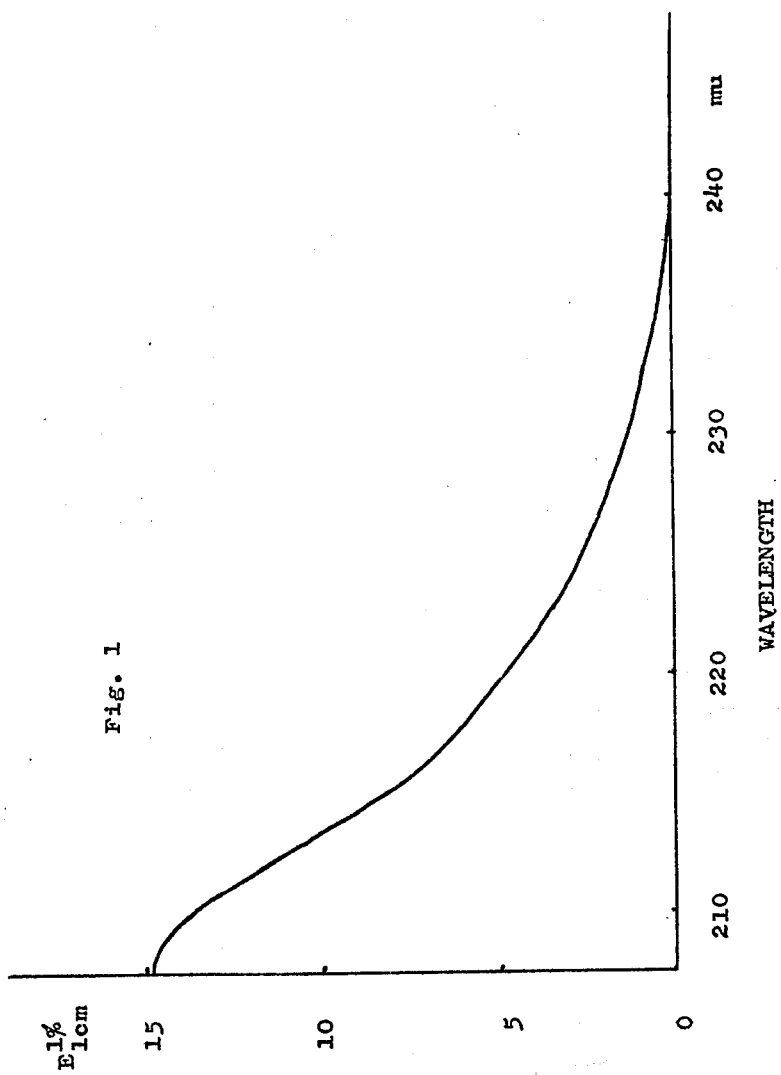
FIG. 1 shows the ultra violet absorption spectrum of TM-481 in methanol.

The new antibiotic, TM-481, of this invention is prepared by the cultivation, under controlled conditions, of a new strain of *Streptomyces ribosidificus* which was identified by a generally known ISP (International Streptomyces Project) method described by Gottlieb and Shirling.

The microbiological properties of the new strain, *Streptomyces ribosidicus* TM481 (ATCC No. 31051) are as follows:

1. General morphological findings

A mycelium is formed with the display of slight curved hyphae on glucose-asparagine agar medium although development of aerial mycelium is poor. But aerial mycelia on oatmeal agar, yeast extract-malt extract agar or starch agar medium form abundant spores.

Microscopic examination of the cultures grown on yeast extract-malt extract agar reveals branched filaments and spore chains forming spiral. Mature spore chains generally contain about 10 spores per chain. Electron micrograph of the spore shows oval to spherical form (0.7–1.0 × 1.0–1.4) with spiny surface.

2. Cultural characteristics

The cultural characteristics of *Streptomyces ribosidificus* TM-481 are listed in Table 1.

TABLE 1

| Medium | Cultural characteristics of *Streptomyces ribosidificus* TM-481 | | |
|---|---|---|---|
| | Growth | Aerial Mycelium | Soluble Pigment |
| Sucrose-nitrate agar | Poor, yellowish cream to yellowish green | Poor, pale yellow | None |
| Glucose-asparagine agar | Poor, colorless to yellowish cream | Powdery, grayish brown | None, pale yellow after 2 weeks |
| Glycerol-asparagine agar | Good, yellowish cream | White to light gray or yellowish green | None |
| Starch agar | Good, yellowish cream to light gray | Abundant, pale yellowish green to dark gray | None |
| Tyrosine agar | Good, yellowish cream | Abundant, white to light gray or pale yellowish green | None |
| Nutrient agar | Poor, colony shape, yellowish cream | None | None |
| Yeast extract-malt extract | Good, grayish yellow to yellowish green | Abundant, pale yellowish green to | None |

TABLE 1-continued

Cultural characteristics of *Streptomyces ribosidificus* TM-481

| Medium | Growth | Aerial Mycelium | Soluble Pigment |
|---|---|---|---|
| agar | | dark gray | |
| Oatmeal agar | Good, yellowish cream to light gray | Abundant, yellowish green to dark gray | None |

All cultures were incubated at 30°C.

3. Physiological properties

The physiological properties of this strain are as follows:

Growth temperature range: 15°–45°C on oatmeal agar,
Optimal growth temperature: 30°–35°C,
Liquefaction of geltatin: slightly positive around the growth in 5–7 days at 20°C,
Hydrolysis of starch: positive,
Coagulation of skimmed milk: negative,
Peptonization of skimmed milk: negative at 30°C, positive at 37°C,
Melanin production: negative,
Liquefaction of Loeffler's coagulated serum: positive, and
Reduction of nitrate: positive.

Carbon source utilization test by method of Pridham and Gottlieb shows that this strain is able to utilize moderately or well D-glucose, L-arabinose, D-fructose, sucrose, inositol, rhamnose, raffinose, and D-mannitol, but not at all D-xylose.

From the above results, the microbiological characteristics of this strain may be summarized as follows:

The strain TM-481 forms aerial mycelium with spiral and spore surface is spiny. Growth on synthetic media is poor and mycelium is yellowish cream to yellowish green. Soluble pigment is not generally observed but the culture on glucoseasparagine agar medium produces pale yellow soluble pigment. Cultures on organic media show good growth with yellowish cream to yellowish green color and abundant spore formation. But soluble pigment is not produced on the media.

These characteristics of the strain TM-481 closely relate with those of Waksman's "flavus" series of Streptomyces. Among the known species of this series, *Streptomyces flavus*, *Streptomyces flaveolus*, *Streptomyces ribosidificus* are similar to the strain TM-481 with respect to the form of spore bearing hyphae and the character of spore surface.

The detailed comparative study of the above species showed that TM-481 resembles particularly *Streptomyces ribosidificus* which produces ribostamycin, an aminoglycoside antibiotic. Main similar characteristics of both strains are, for example, to form spore chain on aerial mycelium with open spiral, generally not to produce any soluble pigment on synthetic agar media or organic media, to be able to grow even at 45°C, relatively high temperature and to have the ability of producing ribostamycin. The different characteristics between both strains is only that TM-481 utilizes fructose and liquefies gelatin but *Streptomyces ribosidificus* does not.

From these features, it was reasonably concluded that the strain of this invention belongs to the species of *Streptomyces ribosidificus*, and so said strain was designated as *Streptomyces ribosidificus* TM-841.

This strain has been deposited to the Institute for Microbiological Industry and Technology, Japan, as FERM-P No. 2267, and at American Type Culture Collection, Rockville, Md. as ATCC No. 31051.

The antibiotic substance TM-481 is usually obtainable by inoculating an aqueous nutrient medium with a culture of the strain of *Streptomyces ribosidificus* TM-481, culturing said strain by the shaking culture method or aerated submerged culture method and separating the thus produced antibiotic TM-481 from the culture medium.

As well as the media in which other microorganisms are grown for the production of antibiotics, the nutrient medium for culturing the strain TM-481 usually contains sources of assimilable carbon and nitrogen. As sources of assimilable carbon, various carbohydrates such as ordinary starch, glycerol and sugars, for example, glucose and sucrose are preferebly used. Various lipids and vegetable or animal oil may be used for the same object. Suitable sources of assimilable nitrogen include a wide variety of substances such as peptone, amino acids, casein, fish meal, soya bean meal, meat extract, yeast extract and various other nitrogenous substances of vegetable or animal origin. Chemicals such as urea nitrates and ammonium compounds may also be added to the nutrient media as a nitrogen source. Corn steep liquor, because of the wide variety of both organic and inorganic substances contained therein, is a valuable additive to the fermentation media. In some cases, essential mineral salts such as sodium chloride or antifoam may be added also.

The pH value of the medium is brought substantially to neutrality before sterilization, preferably to about pH 7. Fermentation is preferably carried out at a temperature of 30°–35°C. The development of the culture is comparatively rapid, and so it can be observed that the active substance was produced in the culture media after 30 hours under suitable aerated submerged culture condition. The maximum production of TM-481 substance is usually attained after 40–44 hours in jar fermentation.

As the most of the produced active substance TM-481 is contained in the broth filtrate, said substance can be separated comparatively easily from the culture medium. Usually, the separation procedure is carried out as follows. After cultivation, mycelia are removed by centrifugation and the objective substance is extracted from the obtained supernate with water-immiscible organic solvents such as ethyl acetate, benzene and chlorform. The extract is then concentrated to dryness. Many impurities can be removed from the obtained oilish residue by extracting the objective substance with a suitable organic solvent.

Moreover, TM-481 can be further purified and isolated by the efficient combination of silica gel column chromatography, gel filtration on Sephadex LH-20 and crystallization using proper organic solvents such as n-hexane and acetone. TM-481 substance can be obtained as white prismlike crystal.

Figure 2:
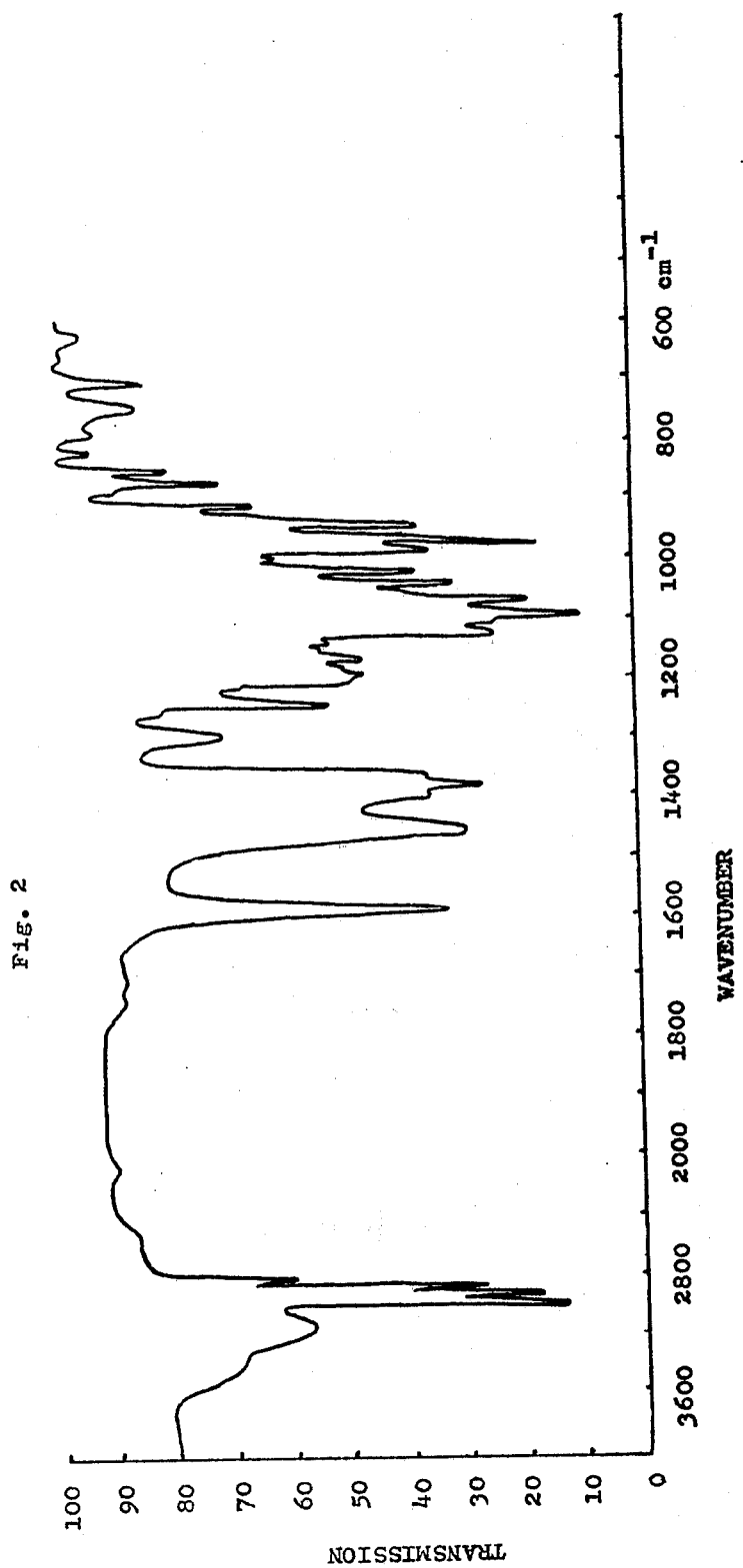
FIG. 2 shows the infrared absorption spectrum of TM-481 with tablet of KBr.
Figure 3:
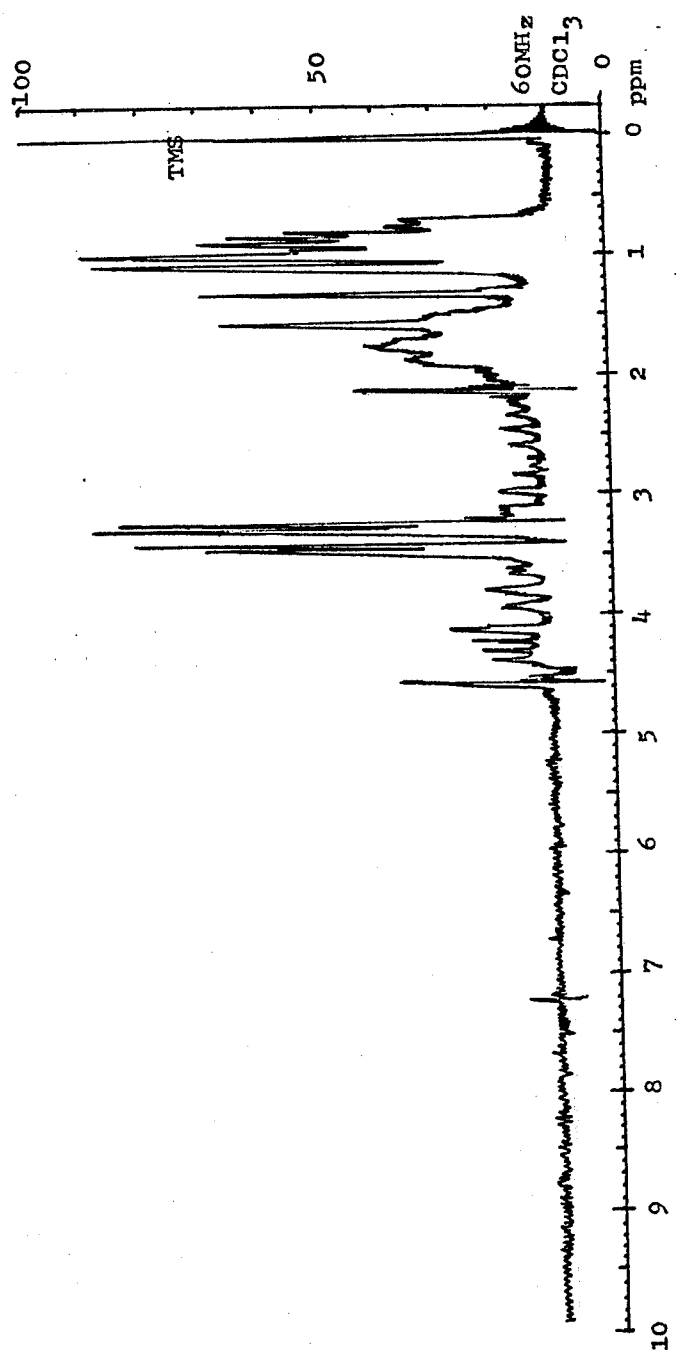
FIG. 3 shows the nuclear magnetic resonance spectrum of TM-481 in deutrochloroform.

Thus obtained antibiotic TM-481 has the following physico-chemical properties:

1. Elemental Analytical Values
   C: 61.93, H: 8.64, O: 26.75, Na: 2.68 (%)
2. Molecular Weight
   about 846 (vapor pressure method)
3. Estimated Empirical Formula
   $C_{42-45}H_{71-75}O_{14-15}Na$
4. Melting Point
   188°–189°C
5. Specific Optical Rotation
   $[\alpha]_D^{25} = +47°$ (C=1%, methanol)
6. Ultra Violet Absorption Spectrum
   The antibiotic TM-481 dissolved in methanol shows only end absorption (FIG. 1).
7. Infrared Absorption Spectrum
   The infrared absorption spectrum determined with tablet of KBr illustrated in FIG. 2 shows characteristic bands at 3400, 3180, 2980, 2940, 2880, 2810, 1590, 1460–1450, 1400, 1385, 1375, 1300, 1240, 1210-1190, 1170, 1140, 1120, 1095, 1075, 1040, 1020, 1000, 985, 965, 940, 915, 890, 870, 865 and 830 cm$^{-1}$.
8. Nuclear Magnetic Resonance Spectrum The nuclear magnetic resonance spectrum at 60 MH$_z$ of TM-481 in CDCl$_3$ shows the characteristic four singlet at δ3.25–3.45 which mean probably four methoxy groups (FIG. 3).

9. Solubility
   TM-481 is soluble in ethyl acetate, benzene, chloroform, methanol, ethanol, acetone, n-hexane, petroleum ether and ethyl ether, and insoluble in water.
10. Color Reaction
    TM-481 gives positive reaction with iodine and potassium permanganate, but negative reaction with ninhydrin, Molish and ferric chloride.
11. Other Property The substance is hardly transferred to aqueous layer from organic solvent layer by extraction in acidic or alkaline range.

TM-481 demonstrates antibacterial activity against pathogenic microorganisms, particularly Gram-positive bacteria, more particularly against varieties of antibiotic-resistant staphylococci. Usually, it shows sufficient activity against said staphylococci in the concentration of 3.13–6.25 μg/ml. It shows, however, no activity against Gram-negative bacteria, fungi and yeast.

The antibacterial activity of TM-481 substance was tested under the standardized conditions by inoculating various microorganisms on heart infusion agar or Sabouraud agar medium containing the pure antibiotic TM-481 in various concentration, and each minimum concentration (MIC) of the antibiotic at which tested microorganisms failed to grow was obtained. The antibacterial spectra of TM-481 thus obtained are shown in the following Table 2. Since the highest concentration of TM-481 employed in this test is 50 μg/ml, MIC value is not precisely stated in the case that MIC apparently exceeds 50 μg/ml.

TABLE 2

| Antibacterial Spectra of TM-481 | | |
|---|---|---|
| Microorganism | MIC (μg/ml) | Medium |
| Staphylococcus aureus 209P | 3.13 | 1 |
| Staphylococcus aureus Smith | 3.13 | 1 |
| Staphylococcus aureua TPR-18 (SA-, PC-, TC-, KM-, CP- and Mac-R) | 6.25 | 1 |
| Staphylococcus aureus TPR-23 (SA-, PC-, TC-, SM-, KM-, CP- and Mac-R) | 6.25 | 1 |
| Staphylococcus aureus TPR-26 (SA-, PC-, SM-, CP- and Mac-R) | 6.25 | 1 |
| Staphylococcus aureus TPR-27 (SA-, PC-, TC-, SM-, KM-, CP- and Mac-R) | 6.25 | 1 |
| Staphylococcus epidermidis TPR-13 (SA-, PC-, CP-, EM- and OM-R) | 6.25 | 1 |
| Staphylococcus epidermidis TPR-14 (PC- and CP-R) | 6.25 | 1 |
| Staphylococcus epidermidis TPR-16 (SA-, PC-, TC- and CP-R) | 3.13 | 1 |
| Staphylococcus epidermidis TPR-25 (SA-, PC-, TC-, SM-, KM-, CP- and Mac-R) | 6.25 | 1 |
| Staphylococcus epidermidis TPR-28 (SA-, PC-, TC-, SM-, KM-, CP- and Mac-R) | 3.13 | 1 |
| Bacillus subtilis | 3.13 | 1 |
| Sarcina lutea | 6.25 | 1 |
| Escherichia coli | > 50 | 1 |
| Proteus vulgalis | > 50 | 1 |
| Aspergillus niger | > 50 | 2 |
| Trichophyton asteroides | > 50 | 2 |
| Candida albicans | > 50 | 2 |
| Saccharomyces cerevisiae | > 50 | 2 |

NOTE:
SA - sulfonamides; PC - penicillin; TC - tetracycline;
SM - streptomycin; KM - kanamycin; CP - chloramphenicol;
EM - erythromycin; OM - oleandomycin,
Mac - all of macrolides; R - resistant strain;
Medium 1 - heart infusion agar medium;
Medium 2 - Sabouraud agar medium By the comparison of the properties of the active substance TM-481 with those of various known antibiotics, said TM-481 seems to belong to the group of the polyether type antibiotics. Its properties, however, apparently differ from those of other polyether group antibiotics such as nigericin, X-537A, X-206, monensin, grisorixin, dianemycin, salinomycin, A-28695A, A-28695B and A-204A. Therefore, it is reasonably concluded that the active substance TM-481 of this invention is a novel polyether group antibiotic. Further, similar to other polyether group antibiotics, said TM-481 is also effective against coccidiosis in chickens.

The following examples illustrate presently preferred embodiments of the invention, but are not intended as a limitation therefo.

EXAMPLE 1

Four liters of an aqueous culture medium containing 1% glucose, 2% oatmeal, 0.3% meat extract, 0.3% sodium chloride and 0.2% calcium carbonate at pH 7.0 is divided into 8 parts and each 500 ml is poured into a 2 liter Sakaguchi flask. The medium is sterilized at 120°C for 15 minutes. After cooling, each medium is inoculated with 10 ml. of culture of *Streptomyces ribosidificus* TM-481 in a 500 ml. Sakaguchi flask. The culture is shaken for 48 hours at 30°C.

Then, 4 liters of the obtained seed culture is transferred into a 250 liter fermenter containing 200 liters of the same aqueous medium. The culture in the fermenter is aerated and agitated for 44 hours at 30°C.

The obtained fermentation broth is centrifuged to remove mycelia. Thereafter, 60 liters of ethyl acetate is added into 180 liters of the supernate and the mixture is agitated for 30 minutes for extraction. Most of the active substance is transferred into ethyl acetate layer. The extract separated from the aqueous layer is concentrated in vacuo below 50°C giving brown syrupy residue. The residue is extracted with each 150 ml of benzene three times and insoluble precipitate is removed by filtration. After the combined filtrate is evaporated to dryness, the obtained residue is extracted twice with each 200 ml of methanol and the extract is concentrated in vacuo. Thus obtained residue is dissolved in 200 ml of 80% ethanol and the active substance in ethanol is extracted three times with each 200 ml of n-hexane. Evaporation of the solvent in the combined extract gives 5 g of the objective TM-481 as crude powder.

EXAMPLE 2

One gram of TM-481 obtained in Example 1 is dissolved in 5 ml of chloroform methanol mixture (60:1). Then, the solution is charged on silica gel column packed with ca. 100 g of Kiesel gel 60 (Merck Co., Ltd.), and eluted with the same solvent mixture. The active fractions are combined and evaporated to dryness. Thus obtained residue is further purified by gel filtration on Sephadex LH 20 with methanol. Evaporation of the combined active fraction gives 500 mg of white powder. The powder is recrystallized from n-hexane-benzene mixture (4:1) to obtain 320 mg. of TM-481 white prism.

What is claimed is:

1. An antibiotic, TM-481 being a prism-shaped crystal; having a melting point of 188°–189°C; containing the elements of carbon, hydrogen, oxygen and sodium in the analytical value of C:61.93, H:8.64, O:26.75, Na: 2.68; having a molecular weight of about 846 and corresponding to the empirical formula $C_{42-45}H_{71-75}O_{14-15}Na$; having the degree of optical rotation $[\alpha]_D^{25} = 47°$ (C=1%, methanol); being soluble in ethyl acetate, benzene, chloroform, methanol, ethanol, acetone, n-hexane, petroleum ether and ethyl ether and insoluble in water; giving positive iodine and potassium permanganate tests and negative Molish and ferric chloride tests and showing the ultra violet absorption spectrum, the infrared absorption spectrum and the nuclear magnetic resonance spectrum as in the attached drawings, FIG. 1, FIG. 2 and FIG. 3, respectively.

2. A process for the production of antibiotic TM-481 which comprises cultivating the microorganism strain *Streptomyces ribosidificus* TM-481 (ATCC No. 31051) in a culture medium containing assimilable carbon and nitrogen sources, extracting the thus produced antibiotic TM-481 from the culture medium with an organic solvent and separating antibiotic TM-481 from the extract solution.

3. A process according to claim 2 wherein the *Streptomyces ribosidificus* TM-481 (ATCC No. 31051) is cultured at a temperature of 30° to 35°C for 40 to 44 hours.

4. A process according to claim 2 wherein the organic solvent is one selected from the group consisting of ethyl acetate, benzene and chloroform.

5. A process according to claim 2 wherein antibiotic TM-481 is separated from the extracted solution by evaporating the extracting solution in vacuo.

* * * * *